(12) United States Patent
Young (10) Patent No.: US 10,702,179 B2
(45) Date of Patent: Jul. 7, 2020

(54) METHOD FOR SENSING ARRHYTHMIA FOR PROVIDING USER FEEDBACK

(71) Applicant: David Young, Bishop, CA (US)

(72) Inventor: David Young, Bishop, CA (US)

( * ) Notice: Subject to any disclaimer, the term of this patent is extended or adjusted under 35 U.S.C. 154(b) by 3 days.

(21) Appl. No.: 16/116,384

(22) Filed: Aug. 29, 2018

(65) Prior Publication Data

US 2019/0076039 A1    Mar. 14, 2019

Related U.S. Application Data

(60) Provisional application No. 62/556,340, filed on Sep. 9, 2017.

(51) Int. Cl.
| | | |
|---|---|---|
| A61B 5/04 | (2006.01) | |
| A61B 5/044 | (2006.01) | |
| A61B 5/0205 | (2006.01) | |
| A61B 5/0472 | (2006.01) | |
| A61B 5/0468 | (2006.01) | |
| A61B 5/024 | (2006.01) | |
| A61B 5/0464 | (2006.01) | |
| A61B 5/1455 | (2006.01) | |
| A61B 5/0245 | (2006.01) | |

(52) U.S. Cl.
CPC ............ *A61B 5/044* (2013.01); *A61B 5/0205* (2013.01); *A61B 5/0472* (2013.01); *A61B 5/02405* (2013.01); *A61B 5/02444* (2013.01); *A61B 5/02455* (2013.01); *A61B 5/0464* (2013.01); *A61B 5/0468* (2013.01); *A61B 5/1455* (2013.01)

(58) Field of Classification Search
CPC .............. A61B 5/0205; A61B 5/02405; A61B 5/02444; A61B 5/02455; A61B 5/044; A61B 5/0464; A61B 5/0468; A61B 5/0472; A61B 5/1455
See application file for complete search history.

(56) References Cited

U.S. PATENT DOCUMENTS

2011/0224565 A1* 9/2011 Ong .................... A61B 5/4824
600/509

* cited by examiner

*Primary Examiner* — Amanda K Hulbert
(74) *Attorney, Agent, or Firm* — Eldredge Law Firm (57) ABSTRACT

A two-dimensional visual display that allows for the user and/or another individual, such as the user's spouse, to experience self-evident, abnormally complex elevated heart rate arrhythmia. The system of the present invention uses a heart rate monitor, along with data analysis, to provide the user with a visual display, seismic feel, and/or aural feedback that allow for the user to be quickly alerted as to any arrhythmia, thereby signaling to the user to change their activity in order to avoid sudden cardiac death.

8 Claims, 5 Drawing Sheets

METHOD FOR SENSING ARRHYTHMIA FOR PROVIDING USER FEEDBACK

BACKGROUND

1. Field of the Invention

The present invention relates generally to arrhythmia collection, presentation systems, and oxygen saturation pulse oximetry ($SpO_2$) sensor presentations, and more specifically, to an arrhythmia displayed self-awareness, awareness of others, and individual pulse oximetry ($SpO_2$) blood oxygen evaluation system that leads to lifestyle evaluation and data processing. The system provides feedback to the user. In addition, the system of the present invention provides a two-dimensional visual display that allows for the user and/or another individual, such as the user's spouse, at a glance, to experience self-evident, abnormally complex elevated heart rate arrhythmia. This visual display, and data analysis of the displayed data, together with the analysis of all the arrhythmia data of any human ECG sensor RR interval output when used with experience and user technology, such as machine learning and pattern recognition skills, the escalation of real-time arrhythmia complexity and elevated heart rate, e.g. [60-140 rate-dispersion], will not result in damage to the user. The user can experience the display visually, "musically", and/or seismically, in real time, where every single real pulse is accounted for.

2. Description of Related Art

Pulse oximetry can provide an early warning of hypoxemia. Lack of oxygen to primary organs such as heart, bran, kidneys is a cause of various ailments. Loss of blood oxygen levels ($SpO_2$) contributes to cardiac arrhythmia, cardiac muscle contractility failure, acute and chronic dementia, and other end organ failure. Therefore, it is important to monitor a person's ($SpO_2$) losses, particularly in regards to arrhythmia (a condition in which the heart beats with an irregular or abnormal rhythm), to ensure that the person remains in a stable and healthy state. It should be appreciated that about 5.7 million adults in the United States have heart failure: 1 in 9 deaths have diagnosed heart failure as the contributing cause. About half of people who develop heart failure die within 5 years of diagnosis. The system of the present invention, including a two-Dimensional Arrhythmia Monitor [hereinafter referred to as 2DAM] Signal Analysis (Intelligence) device, detects and aids in the prevention of a potential cardiac arrest up to 24 hours before the event takes place. The device links oxygen saturation with pulse to pulse heart beats for immediate evaluation by the user. One of the objectives is to save lives through a preventative, self-awareness platform to mitigate the occurrence of pre-mature death through sudden cardiac arrest or SCD.

It is an object of the present invention to use monitoring of two-dimensional arrhythmia (2DAM) with the monitoring of ($SpO_2$) levels, arrhythmias-Heart "Music", and seismic-feel to substantially reduce sudden cardiac arrest and sudden cardiac death for all ages, particularly the vulnerable elderly, leading to prevention of normal cardiac aging.

The 2DAM data mimics the RR period waveforms of conventional ECG data by translating 1D to 2D with machine learning/pattern recognition analysis, and displays & analyzes in real time. These complex waveforms that are ever changing, escalating, and deescalating as the patient participates, resulting in an SCD-Prevention Device. This 2D arrhythmia is presented real time to the patient for typically 1 minute visually, aurally, and/or felt seismically. In combination with pulse oximetry, automatic alerts are based on the patient's requirements, including their doctors-patient pre-determined values, and includes SCD and pre-SCD risk stratification analysis triggers with few false alarms. This SCD-Prevention Device is also an SCD-Risk-Stratification device that will become more sophisticated with machine learning and continued use-time.

Biotronik home monitoring has a similar application, however, there is no real time, 2DAM that the patient can view, hear, or feel. [Biotronik uses the 109-year-old ECG to record heart rhythm.] The FDA approved AF detecting Kardia Mobile has this short-fall also.

In the present invention, an ear-sensor is configured to be used and output could stay in the ear being wirelessly connected elsewhere, visually, heard, and felt to alert the user of the 2DAM ear-sensor's life-saving-prevention findings, and/or data processed and recorded for analysis and linking to the cardiologist.

Traditionally ECGs are sent to the patient's doctor for review, however, the 2DAM when used by the patient in cooperative negotiation with their doctor, gives the opportunity to self-medicate as needed in time critical applications e.g. very small amounts of sotalol [20 mg] can be used in, as little as, 45 minutes before the arrythmia has expanded in amplitude beyond a 60-120 random, increasing rhythm complexity and an even less efficient heart pattern with increasing risk, e.g. 20-140 bpm. Alternatively, the 2DAM used by the practiced resonant breathing person's, typically a 10 second breathing period, often, dramatically, achieves the goal of stress-reduction and subsequent de-escalation of 2DAM heart rate patterns without self-medication.

It should be appreciated that a person typically starts their day at rest, and the work of their heart increases from a lightly worked heart of a sleeping body to increased arrhythmia from a heart with increased workload. This creates a visual display of nearly constant 60 bpm with typically, 3 PAC per 10 second lateral intervals, to tri-levels of 60, 70, 80 bpm, to random patterns from 60 to 100 bpm distributions of heart beats. When a minimal dose of Sotalol or similar anti-arrhythmia medication is applied to both control and limit, the exponential escalation of the arrhythmia is shown.

As activity is increased during the day, arrhythmia is often increased. Rhythms originating from the upper ventricles [Supraventricular Tachycardia] and the lower ventricles [Ventricle Tachycardia], as well. And while arrhythmia may have been recorded on a 12 lead ECG in the doctor's office a week before, these signature rhythms are obviously, not-related. Furthermore, as the complexity of the 2DAM arrhythmia pattern increases with heart workload, the ($SpO_2$) decreases so that, Silent cerebral ischemia (SCI) commonly referred to as vascular dementia, occurs. Cognitive impairment results in addition to increased risk of SCA and SCD.

The implantable cardioverter-defibrillator, ICD is commonly used to prevent SCD, and while the ICD often performs as expected, it is also well known, that the ICD increases the individual's mortality. Shocks reduce long-term heart health. And the shock is not used unless a high-risk rhythm known to trigger SCD, is detected. ICD's are generally implanted by electrophysiologists or other physicians with special training and certification in their placement. The 2DAM includes a wearable that gives an experienced patient, that has completed negotiations with their doctor, the opportunity to anticipate these SCD trigger rhythms and perform prevention with life-style as described, such as stop what you're doing if you are running, resonant breathing, self-medication or go to ER, not waiting until shocked.

Some form of arrhythmia is a commonly felt condition, and there are various types of arrhythmia. Some are harmless, however, it is well known that many are harmful and even deadly. Tachyarrhythmias, defined as abnormal heart rhythms with a ventricular rate of 100 or more beats per minute, can result from a variety of pathologies and are frequently symptomatic. Signs and symptoms related to the tachyarrhythmia most commonly include palpitations or chest discomfort, but may also include shock, hypotension, heart failure, shortness of breath, and/or decreased level of consciousness. Symptoms may be subtler and may include fatigue, lightheadedness, or exercise intolerance. Some patients are truly asymptomatic; this may be more common in nonparoxysmal (incessant) tachycardias. The term paroxysmal supraventricular tachycardia (PSVT) is applied to intermittent SVTs with abrupt onset and offset and a regular ventricular response, in contrast to AF and atrial flutter which have an irregular ventricular response. PSVT occurs with an incidence of 35 per 100,000 persons-years.

Atrial fibrillation (AF) is the most common cardiac arrhythmia that has the following electrocardiographic: (1) The RR intervals follow no repetitive pattern. They have been labeled as "irregularly irregular"; (2) While electrical activity suggestive of P waves is seen in some leads, there are no distinct P waves. Thus, even when an atrial cycle length (the interval between two atrial activations or the P-P interval) can be defined, it is not regular and often less than 200 milliseconds (translating to an atrial rate greater than 300 beats per minute). The 2DAM measures pulse to pulse beats, creating a new image and sensor not seen in an ECG with significant accuracy to alarm the user of deadly arrhythmias in time to use lifestyle modifications to protect life with preservation of heart and brain function.

AF can have adverse consequences related to a reduction in cardiac output and to atrial and atrial appendage thrombus formation. Systemic embolization, and particularly stroke, is the most frequent major complication of AF. In addition, affected patients may be at increased risk for mortality. Although risk factors for the development of atrial fibrillation (AF) have been identified preventive strategies that significantly reduce the risk have not been identified.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Figure 1:
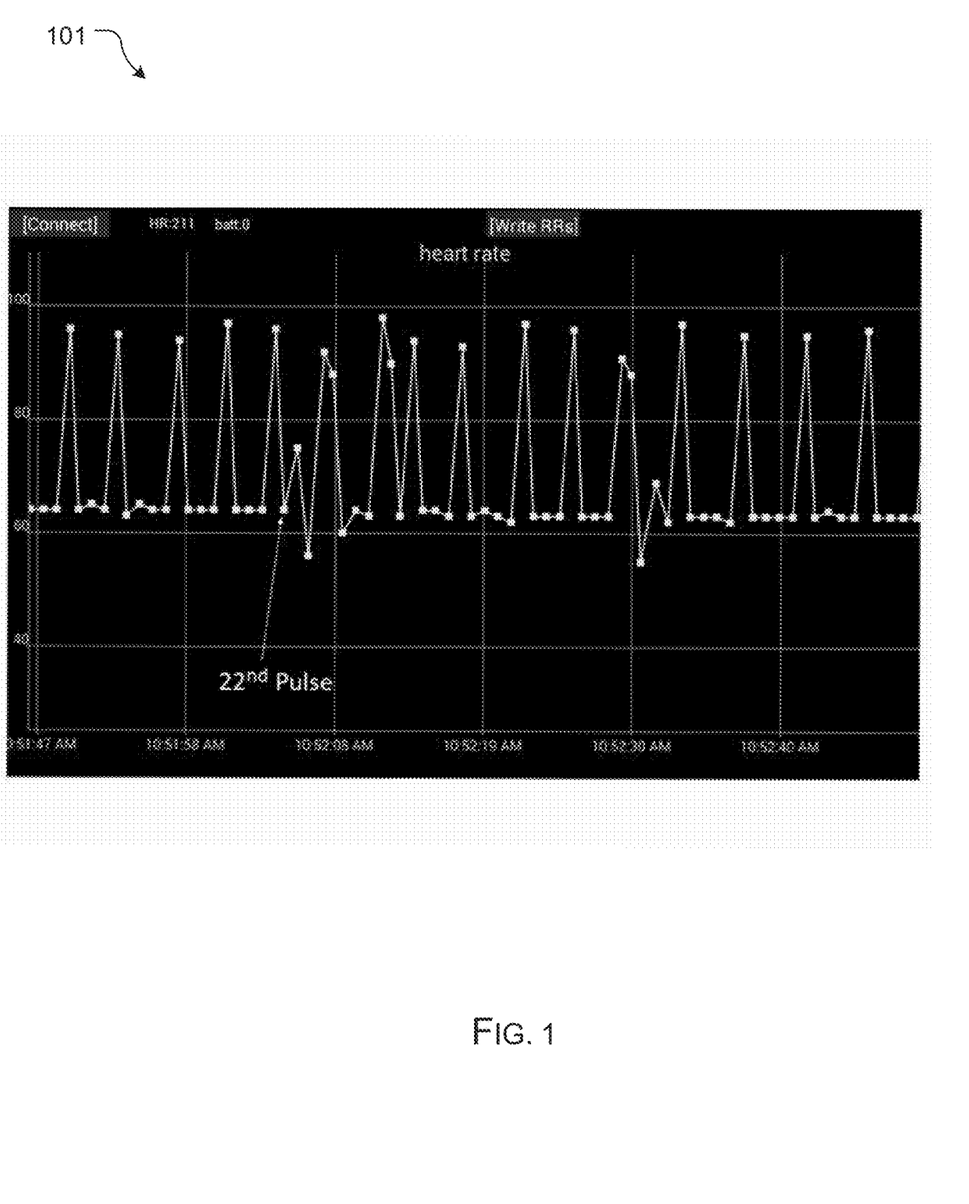
FIG. 1 is a graph that depicts an arrhythmic pulse as correlated to an audio hertz frequency as an example of the present application.

Referring now to the drawings wherein like reference characters identify corresponding or similar elements throughout the several views. FIG. 1 depicts a graph 101 demonstrating the sensitivity of (SpO$_2$) loss that increases from 93% to 92% with an increased degree of arrhythmia complexity described visually and aurally as music, according to various embodiments described herein. Two, 5 second periods of 5 pulse-complexes, i.e. 5 dot-complexes reduce (SpO$_2$). [Times: 10-52; 08 & 10; 52:30] It should be noted that reduction of Oxygen Saturation, (SpO$_2$), Standard is 95-100%, and a reduce level of blood oxygen level may compromise organ function.

The FIG. 1 chart depicts the two-dimensional display, wherein each of the dots presented on the graph provides for precise, and quick visual depiction of the state of the user's heart rate. This feature allows for the user, or an associated person, such as a spouse, to see a slight fluctuation, thereby indicating a dangerous condition. It should be appreciated that this 2D display shows the user exactly where any abnormal heart beat occurs, thereby providing the user with immediate feedback to either reduce their stress, such as through breathing techniques, or possibly self medicate, based on advice from their doctor. This differs from conventional EKGs, in that the user can actually see details, and slight fluctuations, thereby giving them the information they need immediately.

Figure 2:
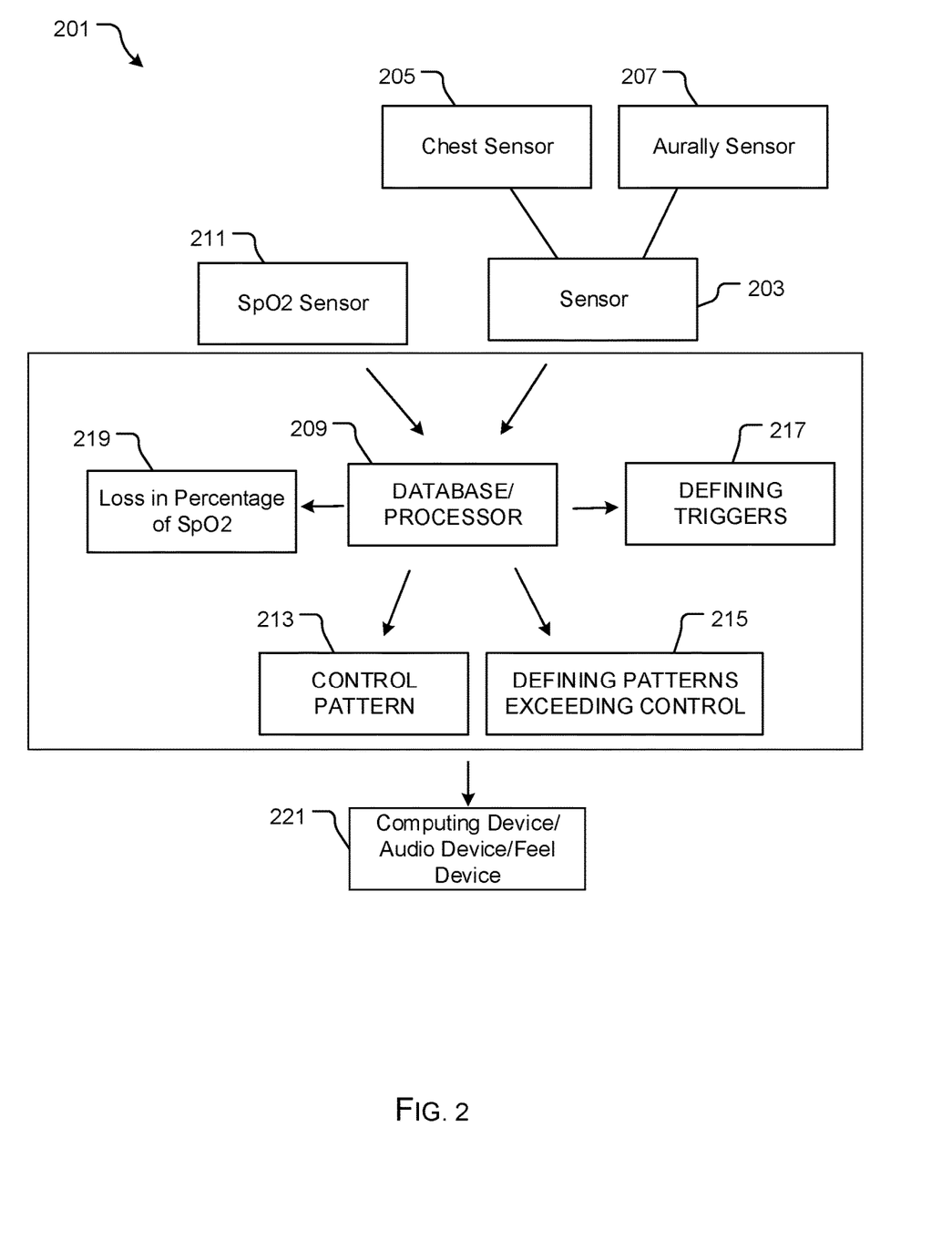
FIG. 2 is a simplified schematic of a system in accordance with a preferred embodiment of the present application.

In FIG. 2, the system 201 of the present invention is shown, wherein a heart rate sensor 203, which can be a chest sensor 205 or aurally engaged sensor 207 are configured to transmit data to a database/processor 209. In addition, an ($SpO_2$) sensor 211 is configured to transmit data to the database/processor 209. It must be understood that the chest sensor 205 or aurally engaged sensor can be any commonly known sensor, or any developed in the future that are configured to collect data.

The data is configured to determine a control pattern 213 and further configured to be used in defining patterns 215 that exceed the control pattern. This information is further used to define triggers 217 and compare with a loss in percentage of ($SpO_2$) 219 in order to provide the user with feedback 221, such as through a computing device (2D display) or audio device (aural feedback), or through a sensor, such as a vibrating sensor to be carried by the user. For example, as the user's arrhythmia increases, the vibrating sensor would vibrate, such as in the user's pocket, to alert the user to the possible risk.

Figure 3:
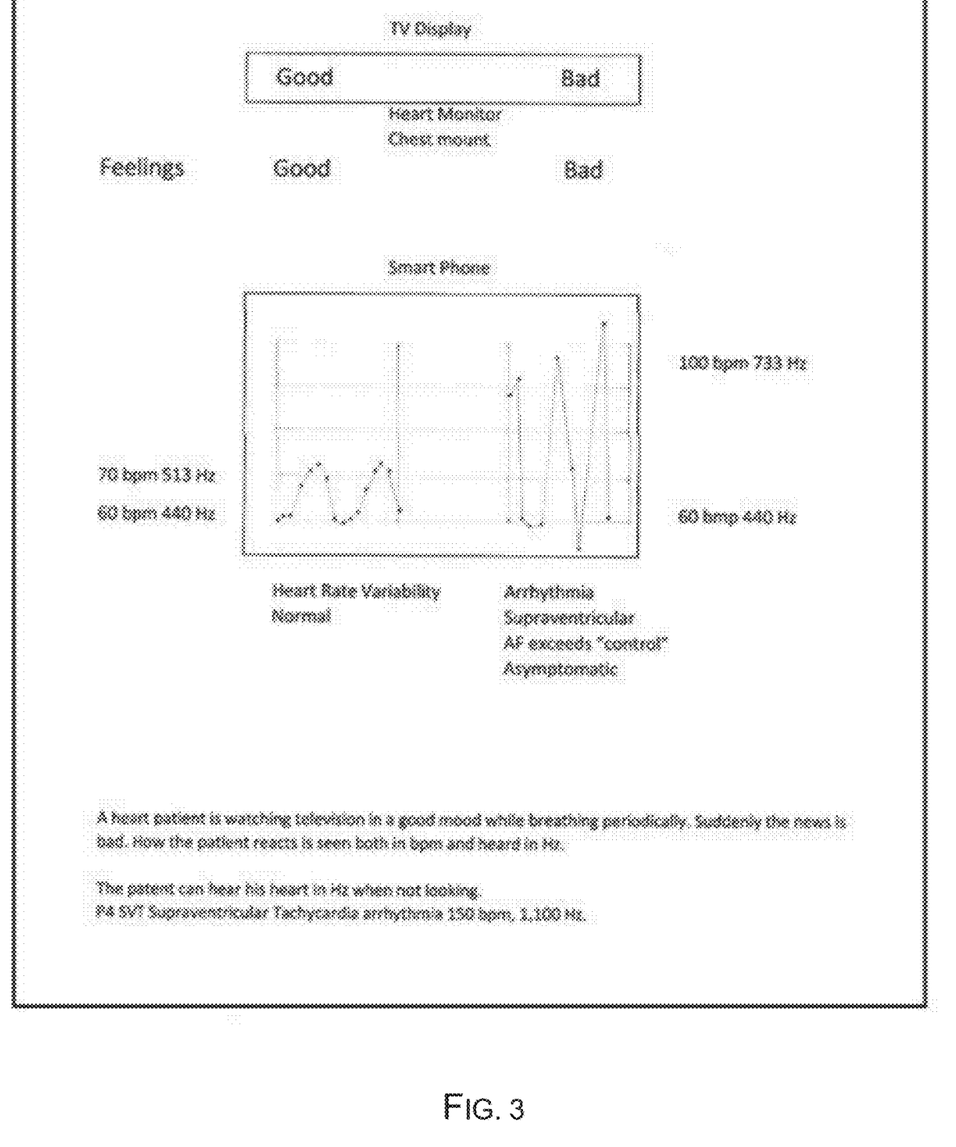
FIG. 3 is an exemplary embodiment of a user display associated with FIG. 2.

As shown in FIG. 3, in one embodiment, the user is presented with a display that provides the user with details as to their state. This display can be configured into an electronic device, such as a TV, cell phone, tablet, or the like, and provides a 2D display that can easily be evaluated by the user. This figure shows the heart rate in hertz vs time with every pulse accounted for. It can be understood that a user will likely be aware of, and have prior knowledge, of a familiar visual pattern from their own approximate translation of the Supraventricular Tachycardia ECG, as they have witnessed through medical treatment, such as with their cardiologist during an office visit. This system creates a visual pattern that can provide alerts that are not seen in a conventional medical treatment setting (during the cardiologist office visit), these alerts are associated with life-limiting arrhythmias. In conventional medical treatment, no prediction method has been found possible to provide the benefits of the present invention, namely the providing of visual alerts to the user upon an arrhythmia detection. In the personal arrhythmogenic environment, altered cardiac physiology leads to new recurrent arrhythmias, improving healthy life-style and subsequent decreasing opportunities for sudden cardiac death.

In some embodiments, wherein the data is translated into music to provide aural feedback to the user, the heart rate in hertz vs time for every pulse may be modified slightly to achieve music where each pulse is a whole note, which produces a pleasant sound and makes imagined familiar visual patterns, like Super Ventricle, easily recognized. Alternatively, each pulse of Music could be, not only a whole note, but be the appropriate sharp or flat note, thus reducing the small hertz error even further. It should be appreciated that the system could include all-note music, including sharps and flats, or could include just whole notes, wherein the average error would be 5.7%.

The 2DAM Ring, the Ring being a standard wearable, sequentially presents in real time 10 second interval peaks and minimum arrhythmia heart rate in bpm for all arrhythmia. For a person at rest with normal rhythm, these two numbers would often be nearly identical, but for a person with dangerous arrhythmia the lower number could be 60 and the upper number 300 bpm, the difference changing greatly or not so much with real time. This large difference and that difference with time is the prevention alert given, visually, aurally, or seismically.

Figure 4:
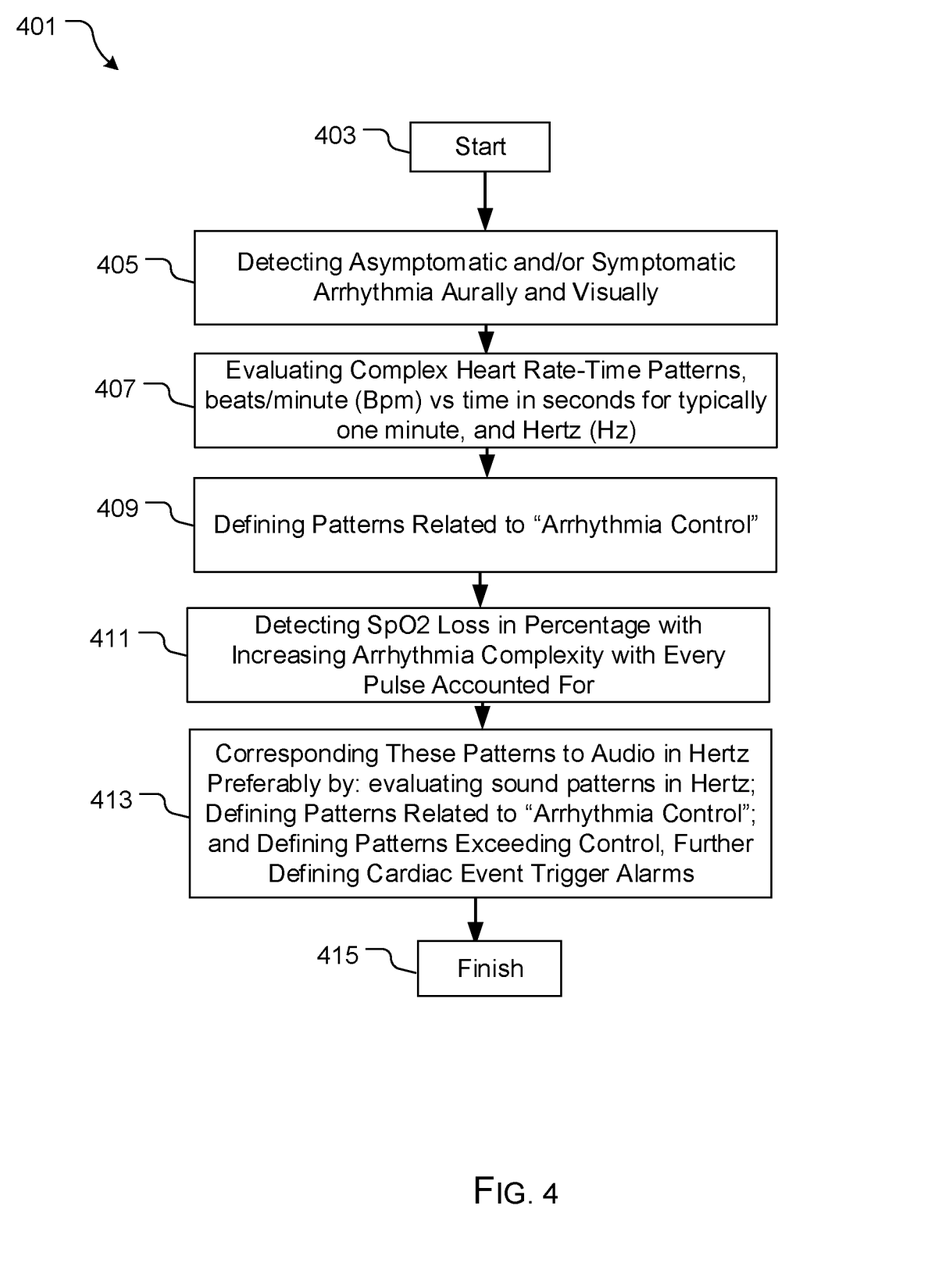
FIG. 4 is a flowchart of the method of the system of FIG. 2 in accordance with a preferred embodiment of the present application.

In FIG. 4, a flowchart depicts the method associated with system 201. During use, first as the processes is started 401, data is collected from a sensor, such as a chest sensor, to determine the user's asymptomatic arrhythmia is detected, either aurally and/or visually, as shown with boxes 403, 405. The data is used to create a control pattern, and further detecting ($SpO_2$) percentage losses, as shown with boxes 407, 409, 411. This data is used to correspond patterns to audio in Hertz, preferably by evaluating sound patterns in Hertz, defining patterns related to arrhythmia control, and defining patterns exceeding control, and further defining 2DAM signature cardiac event trigger alarms, as shown with boxes 413, 415.

In further embodiments, a process of developing self-awareness and awareness of others, encompassing life-style experienced procedures designed to prevent SCD, by evaluating data, using real time, pulse-to-pulse displays of heart-rate-($SpO_2$)-in-% and/or hearing of arrhythmia pulse converted to musical notes. As arrhythmia rate-magnitude-complexity increases beyond controlled AF, while remaining asymptomatic, experienced risk increases exponentially and can lead to death without awareness. 2DAM unique signature occurs before sudden cardiac death.

In some embodiments the process may include the steps of: detection of Asymptomatic arrhythmia aurally and visually; evaluating non-linear complex heart rate-time patterns, beats/minute Bpm, and Hertz Hz; define patterns related to "Arrhythmia Control"; define patterns exceeding "Control", further defining cardiac event triggers & trigger risk; define patterns inside "Control", encouraging behavior, reducing stress and reducing risk of cardiac event; detecting ($SpO_2$) Loss in % with increasing arrhythmia complexity; correspond these patterns to audio in hertz; evaluate sound patterns in Hertz; define patterns related to "Arrhythmia Control"; define patterns exceeding Control, further defining cardiac event trigger alarms; define patterns inside "Control", encouraging behavior, reducing stress and reducing event risk; and audio patterns associated with visual ($SpO_2$) losses will become aural alarms with dual sensor experience.

It should be appreciated that an ear sensor provides arrhythmia music to the inner ear of the user initially without going anywhere externally to the ear. Alternatively, an ear sensor can be electronically connected, such as via Bluetooth or WiFi, to an electronic device, such as a smart phone, or other device, wherein either visual or audio arrhythmia can be utilized. This allows for the user to adjust life-style. If the patient does not reduce his anxiety or if he should add more stress for some other reason, a higher tone with increased volume and/or distortion could be added to create an alarm.

It should be appreciated that one of the unique features believed characteristic of the present application is the use of sensors configured to detect arrhythmia, and ($SpO_2$) percentage drop, to provide the user with feedback, thereby allowing the user to receive feedback prior to being symptomatic, and therefore the user can alter their activity as needed.

Figure 5:
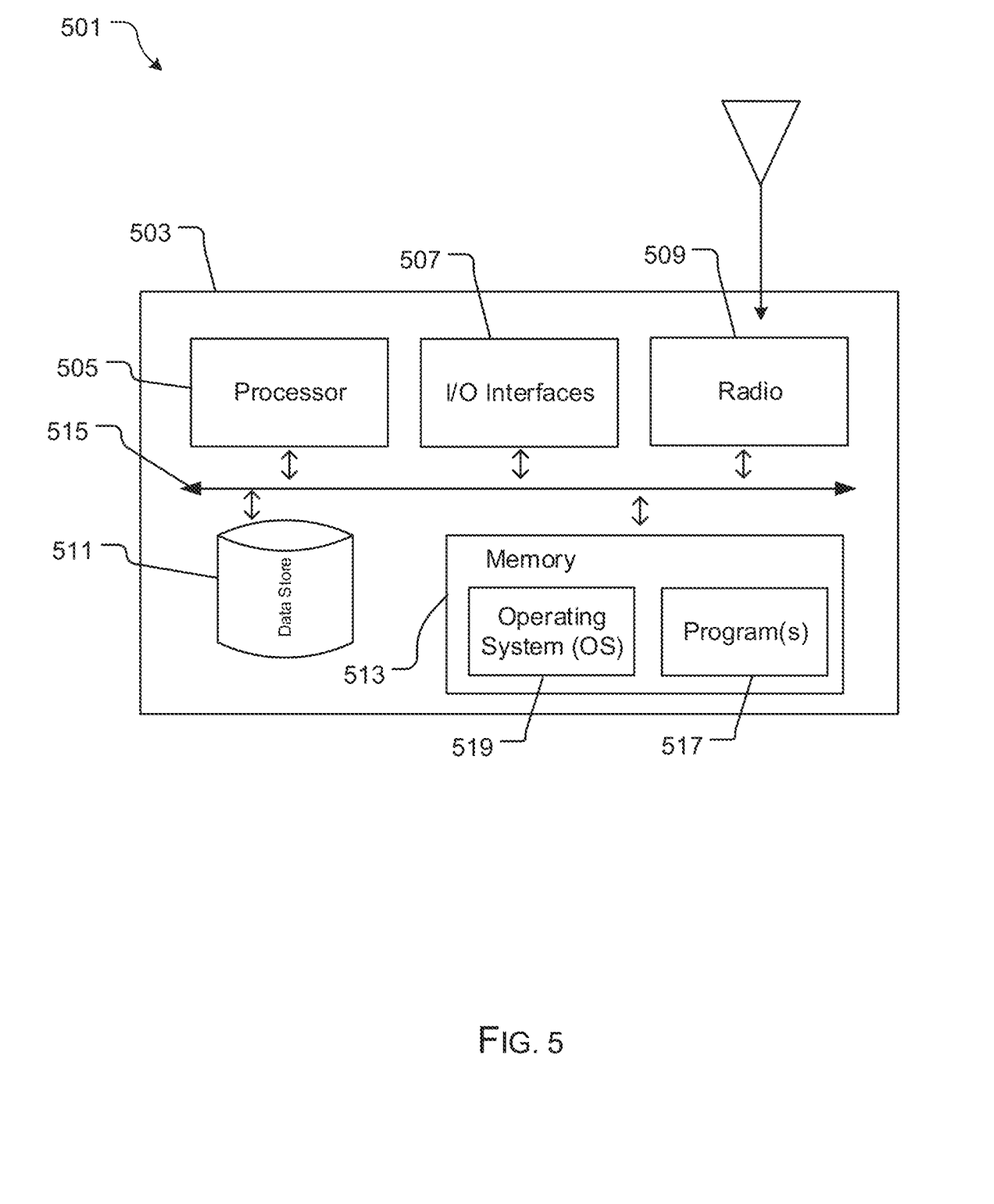
FIG. 5 is a block diagram of an example of an electronic device in accordance with one embodiment of the present application.

Referring to FIG. 5, in an exemplary embodiment, a block diagram 501 illustrates an electronic device 503, which may be used in the system. The term "electronic device" as used herein is a type of electronic device comprising circuitry and configured to generally perform functions such as recording audio, photos, and videos; displaying or reproducing audio, photos, and videos; storing, retrieving, or manipulation of electronic data; providing electrical communications and network connectivity; or any other similar function.

The electronic device 503 can be a digital device that, in terms of hardware 509, generally includes a processor 505, input/output (I/O) interfaces 507, a radio 509, a data store 511, and memory 513. It should be appreciated by those of ordinary skill in the art that FIG. 5 depicts the electronic device 503 in an oversimplified manner, and a practical embodiment may include additional components and suitably configured processing logic to support known or conventional operating features that are not described in detail herein. The components are communicatively coupled via a local interface 515. The local interface 515 can be, for example but not limited to, one or more buses or other wired or wireless connections, as is known in the art. The local interface 515 can have additional elements, which are omitted for simplicity, such as controllers, buffers (caches), drivers, repeaters, and receivers, among many others, to enable communications. Further, the local interface 515 may include address, control, and/or data connections to enable appropriate communications among the aforementioned components.

The processor 505 is a hardware device for executing software instructions. The processor 505 can be any custom made or commercially available processor, a central processing unit (CPU), an auxiliary processor among several processors associated with the electronic device 503, a semiconductor-based microprocessor (in the form of a microchip or chip set), or generally any device for executing software instructions. When the electronic device 503 is in operation, the processor 505 is configured to execute software stored within the memory 513, to communicate data to and from the memory 513, and to generally control operations of the electronic device 503 pursuant to the software instructions. In an exemplary embodiment, the processor 505 may include a mobile optimized processor such as optimized for power consumption and mobile applications. The I/O interfaces 507 can be used to receive user input from and/or for providing system output. User input can be provided via, for example, a keypad, a touch screen, a scroll ball, a scroll bar, buttons, bar code scanner, and the like. System output can be provided via a display device such as a liquid crystal display (LCD), touch screen, and the like. The I/O interfaces 4404 can also include, for example, a serial port, a parallel port, a small computer system interface (SCSI), an infrared (IR) interface, a radio frequency (RF) interface, a universal serial bus (USB) interface, and the like. The I/O interfaces 507 can include a graphical user interface (GUI) that enables a user to interact with the electronic device 503. Additionally, the I/O interfaces 507 may further include an imaging device, i.e. camera, video camera, etc.

The radio 509 enables wireless communication to an external access device or network. Any number of suitable wireless data communication protocols, techniques, or methodologies can be supported by the radio 509, including, without limitation: RF; IrDA (infrared); Bluetooth; ZigBee (and other variants of the IEEE 802.15 protocol); IEEE 802.11 (any variation); IEEE 802.16 (WiMAX or any other variation); Direct Sequence Spread Spectrum; Frequency Hopping Spread Spectrum; Long Term Evolution (LTE); cellular/wireless/cordless telecommunication protocols (e.g. 3G/4G, etc.); wireless home network communication protocols; paging network protocols; magnetic induction; satellite data communication protocols; wireless hospital or health care facility network protocols such as those operating in the WMTS bands; GPRS; proprietary wireless data communication protocols such as variants of Wireless USB; and any other protocols for wireless communication. The data store 511 may be used to store data. The data store 511 may include any of volatile memory elements (e.g., random access memory (RAM, such as DRAM, SRAM, SDRAM, and the like)), nonvolatile memory elements (e.g., ROM, hard drive, tape, CDROM, and the like), and combinations thereof. Moreover, the data store 511 may incorporate electronic, magnetic, optical, and/or other types of storage media.

The memory 513 may include any of volatile memory elements (e.g., random access memory (RAM, such as DRAM, SRAM, SDRAM, etc.)), nonvolatile memory elements (e.g., ROM, hard drive, etc.), and combinations thereof. Moreover, the memory 513 may incorporate electronic, magnetic, optical, and/or other types of storage media. Note that the memory 513 may have a distributed architecture, where various components are situated remotely from one another, but can be accessed by the processor 505. The software in memory 513 can include one or more software programs 517, each of which includes an ordered listing of executable instructions for implementing logical functions. In the example of FIG. 5, the software in the memory 513 includes a suitable operating system (O/S) 519 and programs 517. The operating system 519 essentially controls the execution of other computer programs, and provides scheduling, input-output control, file and data management, memory management, and communication control and related services. The programs 517 may include various applications, add-ons, etc. configured to provide end user functionality with the electronic device 503. For example, exemplary programs 4416 may include, but not limited to, a web browser, social networking applications, streaming media applications, games, mapping and location applications, electronic mail applications, financial applications, and the like. In a typical example, the end user typically uses one or more of the programs 517 along with a network such as the system.

The 2DAM, using a common Wearable watch, is a highly specialized sensor-system that avoids SCA/SVD for all ages, from young athletes with unexpended arrhythmia to the elderly with known continuous arrhythmia, extending the function to ($SpO_2$) estimates for extended arrhythmia, finally providing standard date-time. [Cell phone use, advertising, app selection and google search typically included in Wearable Watches, are not included to avoid distraction from prevention.] A visual display, musical sound, and seismic feel are the keys to prevention. Two or three seconds of standard PQRST ECG are available with a click at any time.

The 2DAM ($SpO_2$) self-monitoring is an indication of how much blood is pumped into the body, thus controlling the loss of brain function and possible organ loss as well. The 2DAM patient records their escalating arrhythmia simultaneously with reduction in ($SpO_2$) in percent as often as practical for some time, accumulating a memory from which an algorithm provides the patient an approximate incident ($SpO_2$) percent value displayed digitally on an active 2DAM real-time active visual display, so the patient can gage escalation of arrhythmia and simultaneous reduction in ($SpO_2$), without having to have a ($SpO_2$) sensor present at the time.

Since 2DAM patients often need tablets that stay on, a 2DAM application for their display is provide with an option to override the limited display-off option the Tablets have.

This is an Algorithm to distinguish normal ECG from unique 2DAM patterns. For example, when watching ECG from arrhythmia to death, the displayed arrhythmia contains only periodic, reasonably formed, somewhat periodic, PQRST waveforms on the ECG. The ECG simply shows a very high, chaotic heart rate that could be confused with a non-lethal arrhythmia. 2DAM verifies a flat line arrhythmia, the 2DAM signature, that occurs while the heart still has the power to recover and well before the ECG loses all of its wave forms. When ventricular tachycardia leads to ventricular fibrillation, SCA occurs, then SCD results, without attention, in minutes. Little or no blood being pumped to the body, but a normal ECG, when followed to death or a flat line ECG, is preceded by a unique 2DAM signature coupled with a reduction in oxygen saturation ($SpO_2$), this algorithm assures unique 2DAM arrhythmia is still pumping some blood and SCA is not taking place at that time. An alert is provided for immediate intervention such as supplemental oxygen as well as resonant breathing.

Only the human in cooperation with their doctor, using the 2DAM, with ECG QRST detail, occasionally, Prevent SCA/SCD. And only the patient in cooperation with their doctor can self-medicate and calmly receive the alert then stop, look, and listen in time to live a cardiac healthy life-style, making this a new process of cardiac study with the potential of extending life for many.

evaluate normal ECG or 2DAM patterns so that the displayed arrhythmia contains only periodic, reasonably formed, somewhat periodic, PQRST waveforms that are verified to be arrhythmia. When ventricular tachycardia leads to ventricular fibrillation, SCA occurs, then SCD results, without attention, in minutes: Little or no blood being pumped to the body, but a normal ECG or 2DAM simply shows a very high, chaotic heart rate that could be confused with displayed arrhythmia. This algorithm assures arrhythmia is pumping some blood and SCA is not taking place at that time. An alert is provided.

Only the human in cooperation with their doctor, using the 2DAM, with ECG QRST detail, occasionally, Prevent SCA/SCD. And only the patient in cooperation with their doctor can self-medicate and stop look listen in time to live a cardiac healthy life-style, making this a new process of cardiac study with the potential of extending life for many.

It should be appreciated that there are various known heart monitors currently available, many of which could be incorporated into the present invention.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A method for sensing arrhythmia and providing arrhythmia feedback to a user, the method comprising:
   detecting arrhythmia via a heart sensor when the user is either asymptomatic or symptomatic;
   evaluating heart rate patterns based on data collected from the heart sensor, the data including beats per minute;
   converting the data collected from the heart sensor, including beats per minute to audio data;
   defining an arrhythmia control pattern based on the data collected from the heart sensor, the arrhythmia control pattern being associated with an asymptomatic arrhythmia of the user;
   defining one or more patterns from the data collected from the heart sensor that exceed the arrhythmia control pattern, thereby indicating arrhythmia outside of the control pattern;
   defining cardiac event triggers based on the arrhythmia control pattern and the one or more patterns and creating a database of cardiac event triggers;
   providing the user with a two-dimensional display; and
   providing the user with physical feedback based on the one or more patterns, the arrhythmia control pattern, and the cardiac event triggers, the physical feedback being one of audio feedback, visual feedback, or vibrational feedback and the physical feedback being an indication of one of the cardiac event triggers such that the user is altered to a cardiac event;
   wherein the feedback provides the user with details to change their behavior to reduce stress, and further to reduce a risk of sudden cardiac arrest (SCA), silent cerebral ischemia (SCI), and/or sudden cardiac death (SCD).

2. The method of claim 1, wherein the heart sensor is a chest sensor.

3. The method of claim 1, wherein the heart sensor is an aural sensor.

4. The method of claim 1, further comprising:
   transmitting the audio data to an ear sensor to relay the audio to the user's inner ear.

5. The method of claim 1, further comprising:
   detecting $SpO_2$ levels through an $SpO_2$ sensor and logging $SpO_2$ data collected;
   wherein the $SpO_2$ data can be used to determine a change in $SpO_2$ levels associated with arrhythmia.

6. The method of claim 1, further comprising:
   displaying, in real-time, a pulse-to-pulse display of heart rate and $SpO_2$ levels to the user on a computing device.

7. The method of claim 1, further comprising:
   encouraging behavior via a computing device to the user to aid in reducing stress.

8. The method of claim 1, further comprising:
   corresponding the one or more patterns and the arrhythmia control pattern to seismic-feel to the user via a vibration sensor to be carried by the user.

* * * * *